United States Patent [19]
Hudson

[11] Patent Number: 6,132,754
[45] Date of Patent: Oct. 17, 2000

[54] METHOD FOR HELPING A PATIENT ELIMINATE TOBACCO DEPENDENCY

[76] Inventor: Paul J. Hudson, 3725 W. Grace St., Tampa, Fla. 33607

[21] Appl. No.: 09/255,977

[22] Filed: Feb. 23, 1999

[51] Int. Cl.⁷ ....................................................... A61F 2/02
[52] U.S. Cl. .............................................................. 424/423
[58] Field of Search ................................................ 424/423

[56] References Cited

U.S. PATENT DOCUMENTS 4,555,397  11/1985  Bachynsky .............................. 514/557

*Primary Examiner*—Carlos A. Azpuru

[57] ABSTRACT

Individuals are aided in their desire to stop tobacco smoking by combining medications and behavioral therapy. The combination addresses the physical and emotional displeasure of nicotine withdrawal, so that individuals addicted to tobacco smoking can experience a more comfortable method in which to quit smoking.

13 Claims, No Drawings

METHOD FOR HELPING A PATIENT ELIMINATE TOBACCO DEPENDENCY

BACKGROUND OF THE INVENTION

Field of the Invention

The field of invention relates to a method for helping a patient eliminate tobacco and nicotine dependency, and more particularly pertains to a new and improved method wherein a patient is injected with a solution of medication, prescribed anticholinergic medications, Medial Forebrain Bundle (MFB) antagonist or agonists and instructed on behavioral therapy which is designed to specifically allow said patient to experience physical and emotional pleasure, so that said patient can quit smoking.

Nicotine, like many other forms of addiction, has both physical and emotional components. The physical side is brought about by nicotine's interference with certain necessary neurotransmitters, specifically "acetylcholine". Nicotine is a congener to the neurotransmitter acetylcholine. It competes to occupy the same receptor sites; specifically the muscarinic sites. Through the process of tolerance, there is a marked increase in the levels of acetylcholine and the number of receptor sites may be increased as well. "Muscarinic stimulation of ganglia and the adrenal medulla usually is thought to be modulatory to nicotine stimulation. The actions of acetylcholine and its congeners at muscarinic receptors can be blocked by atropine. When given parenterally, quaternary ammonium derivatives of atropine and scopolamine are, in general, more potent then their parent compounds both in muscarinic receptor and ganglionic blocking activity: they lack Central Nervous System Activity (CNS) because of poor penetration into the brain". Goodmans & Gillmans: *The Pharmacological Basis of Therapeutics*. 9th Edition The emotional side of nicotine addiction is brought about neurobiologically. The neurobiological process of nicotine addiction is similar to that of other drugs and involves an area of the brain known as the medial forebrain bundle (MFB). This is the reward system of the brain. The structure of the MFB are the frontal cortex, the nucleus accumbens (NA) and the ventral tegmental area (VTA). Nerve fibers running from the VTA to the NA are known as the mesolimbic dopaminergic pathway. These nerves release dopamine in the NA. Dopamine is a neurotransmitter which excites neurons in the NA generating the drive to repeat the brain reward through eating, drinking and sex. The natural drives: eating, drinking and copulation produce this positive reinforcement (i.e. brain reward) encouraging continuation of that behavior. *Smoking and Illicit Drug Use*: Mark S. Gold. M.D. Editor Neurobiological changes are reinforced through years of habitual nicotine abuse. A 1992 article (Cost Effectiveness of Treating Nicotine Dependence) The Mayo Clinic clearly revealed that pharmacotherapies coupled with Behavioral Modification produced efficacy rates in smoking cessation by as much as 47%. Virtually all pharmacological based therapies (i.e. Nicotine Replacement Systems, the patch, gum and antidepressants) include some type of behavioral suggestions as part of their instruction. Since all human behavior is directed by pleasure or pain, a pleasurable cessation period is the preferred modality in replacing MFB stimulation and the maladaptive behavior.

DESCRIPTION OF THE PRIOR ART

The Surgeon General has labeled nicotine as the number one cause of preventable death in the United States. Each year an estimated 435,000 Americans die from smoking related illnesses. Nicotine is responsible for more morbidity and morality than all illicit substances combined. The average smoker smokes for a period of nineteen years and will make eleven attempts at cessation before becoming successful.

Numerous methods to eliminate tobacco dependency have been used including hypnotism, psychotherapy, electro-shock, smoke-free cigarettes, nicotine patches, and group counseling. Prescribed medication has also been utilized to help the smoker quit.

For example, U.S. Pat. No. 4,555,397 to Bachynsky sets forth a method to help a patient stop smoking by injecting a patient with a solution of atropine and scopolamine, potentiated by chlorpromazine to help the patient alleviate the withdrawal symptoms associated with nicotine addiction.

U.S. Pat. No. 4,255,439 to Cooper sets forth a means and method for aiding individuals to stop smoking by administering internally a combination of medications.

U.S. Pat. No. 5,656,255 to Jones sets forth a nicotine containing spray for administration to the nasal mucosa of an individual to assist the individual in the desire to smoke tobacco.

U.S. Pat. No. 4,959,380 to Wilson sets forth a method to treat people to stop smoking by means of psychologically creating a reaction to the appearance of the cigarettes, so that smokers' lose all interest in smoking.

However, it may be appreciated that there continues to be a need for a method for helping a patient eliminate tobacco dependency embodied in the present invention which combines medication and behavioral therapy in a systematic way to provide a more effective method than those previously known in the prior art. The patient invention addresses the problems presented in the prior art, as well as addresses the patient's physical and emotional displeasure from nicotine withdrawal. The present invention permits a much more comfortable method to stop smoking and in this respect, the present invention substantially fulfills a need not previously completely provided for in the prior art.

SUMMARY OF THE INVENTION

In view of the foregoing disadvantages inherent in the known types of methods to help a patient eliminate tobacco dependency, the present invention provides medications to block the nicotine receptor sites; medications that further calm the reward center of the brain; and, therapy to replace the neuroaccociations of smoking.

The emotional side of nicotine addiction involves the area of the brain known as the medial forebrain bundle. This side the reward system of the brain. Inside the medial forebrain bundle are nerve fibers which release dopamine which excites the reward system of the brain. For instance, the natural drives of eating, drinking, and having sex are produced here. Thus, the present invention addresses the patient's emotional needs as well physical and behavioral needs.

The prevention of nicotine withdrawal symptoms and the replacement of the psychological aspects of nicotine addiction require three separate and distinct courses of medical intervention. By providing medications that (1) block nicotine receptor sites, (2) calm the reward center of the brain and (3) therapy to replace the neuroassociations of smoking, you significantly reduce the rate of recidivism as compared to any of these medical interventions applied individually. (1) Specific compounds of anticholinergic medications, given parenterally, provide the initial blockade of nicotine receptor sites, thus providing immediate relief to the nicotine withdrawal syndrome. Injection sites are both inter muscular and in the area of the mastoid; are subcutaneous. These sites allow for rapid onset and peripheral blockade because the tributaries of the veins in the auricular area contain no valves. Anticholinergics provide the initial blockade of nicotine receptor sites and will remain in effect for a period of 12 to 18 hours.

Oral anticholinergics and scopolamine patches sustain low levels of anticholinergic activity and blocking affinity at nicotinic receptor sites. However, they lack Central Nervous System Activity (CNS) because of poor penetration into the brain.

(2) Benzodiazepines suppress CNS activity, thereby providing relief from reduced dopamine synthesis brought on by the lack of nicotine stimulation. Benzodiazepines are preferred in smoking cessation for the ability to reduce anxiety levels, hypnotic qualities and short half life. Likewise, agonists of MFB stimulation may achieve comparable results.

(3) Implementation of behavioral therapy designed specifically for nicotine addiction allows the patient to experience physical and emotional pleasure during the cessation period. The brain experiences cessation and pleasure as one collective experience and allows change to occur naturally.

This behavioral therapy consists of the identification and interruption of idiosyncratic behaviors as well as physical and emotional patterns. The altered state of consciousness is then reinforced with physical and emotional pleasure.

The invention resides not in any one of these features per se, but rather in the particular combination of all of them herein disclosed and claimed and it is distinguished from the prior art in this particular combination of all its combination for the functions specified.

There has thus outlined, rather broadly, the imprint features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for designing of other means, methods and systems for carrying out the several purposes of the present invention. It is important, therefore, that the claims be regarded as including such equivalent methods insofar as they do not depart from the spirit and scope of the present invention.

Further, the purpose of the foregoing abstract is to enable the U.S. Patent and Trademark Office and the public generally, and especially the scientists, engineers and practitioners in the art who are familiar with patent or legal or medical terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved method of helping a patient eliminate tobacco dependency which has all the advantages of the prior art and none of the disadvantages.

It is another object of the present invention to provide a new and improved method of helping a patient eliminate tobacco dependency which may be easily and efficiently implemented and marketed.

It is a further object of the present invention to promote a new and improved method of helping a patient eliminate tobacco dependency which addresses the problems of the prior art.

An even further object of the present invention is to provide a new and improved method of helping a patient eliminate tobacco dependency which addresses both a patient's physical and emotional need, so that the patient can more easily handle the displeasure associated with nicotine withdrawal. Accordingly, such method of helping a patient eliminate tobacco dependency is effective for the patient.

Still yet another object of the present invention is to provide a new and improved method of helping a patient eliminate tobacco dependency which permits the patient to more comfortably stop smoking.

These together with other objects of the invention, along with the various features of novelty which characterize the invention, are pointed out with particularity in the claims annexed to and forming a part of this disclosure. For a better understanding of the invention, its operating advantages and the specific objects attained by its use, reference should be made to the description matter which is illustrated in the preferred embodiments of the invention.

DESCRIPTION OF THE PREFERRED EMBODIMENTS

Patients are seen at a medical facility dedicated exclusively to the research and treatment of Tobacco Dependency Disorder. Preliminary to receiving any medications, patients completed a medical history and a Fagerstrom Tolerance Questionnaire.

Patients are then subjected to a behavioral modification session and in some cases multiple sessions. The behavioral therapy is designed specifically for smoking cessation in a multi-step process. The need to design this protocol is precipitated by the virtue that most forms of therapy deal with symptoms that are unrelated to those experienced by smokers. Smokers have neuroassociations that may be triggered by a variety of stimuli. (i,e, waking up, driving in the car, talking on the telephone, etc.)

The last decade has brought significant changes in the areas of human development and behavioral modification therapies. Whether you are discussing Gestalt Therapy, Ericksonian Hypnosis, Freudian Psychoanalysis, Neuro Linguistic Programming or other established forms of therapy, they all have one thing in common. Change happens in an instant. It's commonly referred to as a breakthrough. The difference in therapies is the approach and how long it takes to arrive at the breakthrough.

This approach offers many advantages over other forms of therapy. First, behaviors can be targeted, new methods can be readily explained, and results can be easily and immediately evaluated. Second, the protocol offers economy of time and effort. It is easily integrated into daily routines and is under the self-control and monitoring of the individual patient. Third and most important, results are achieved in a short period of time. For people who are quitting, this means faster relief of personal distress.

There are literally thousands of research publications dealing with the systematic application of behavior modification techniques in the successful treatment of maladaptive behavior of individuals. Unlike other therapeutic techniques that deal with exploring inner conflicts or attempting to change the way a person thinks, behavior modification focuses on what the patient does. This approach attempts to change behavior directly by manipulating environmental contingencies through reward or punishment. This therapy consists of a three-step behavioral modification process.

Step One:

Cognitive Reconstruction

Interrupt Physical & Emotional Routines

Give examples of idiosyncratic or habitual patterns (physical and emotional) that humans have.

The use of hypnotic suggestions and presuppositions, instruct patients to change there physical routines from the time they get up and to design and focus on a new set of self talk questions stated in the positive.

Step Two: Reconstructing cognition's underlying resistance

Experience Physical Pleasure

Instruct patients to stay active, engage in physical activities and or exercise. Patients are to focus on a healthy diet to promote optimal digestion and maximum energy.

Experience Emotional Pleasure

Patients are instructed to set aside time daily to engage in activities that derive personal pleasure for them. This daily reward system may consist of activities or other personal indulgences.

Step Three: Core Transformation:

Neuroassociations of the new pleasures are combined with the new experiences and the maladaptive behavior is replaced.

Once the session is complete patients received an EKG and pulmonary lung function test. Physicians perform a physical examination to rule out any contraindications and insure the overall safety of the procedure. Contraindications would include those consistent with the use of anticholinergics; Cardio arrhythmia, bladder dysfunction, narrow angle glaucoma, prostatic hypertrophy and pregnancy.

A standard 3.0 cc solution is prepared in advance. The solution is comprised of 0.4 mg Atropine, 0.4 mg Scopolamine, 12.5 mg Chlorpromazine and 0.5 cc Xylocaine (2%). The standard mixture may be titrated to accommodate age, weight, physical constitution and level of addiction. Typically, a therapeutic dose would range from a total of 1.8 cc to 3.0 cc. For patients of substantial size, level of addiction or who had experienced higher than expected levels of withdrawal symptoms, the amounts of atropine and chlorpromazine may be increased at this time with a secondary inter muscular injection from about 0.1 mg to 0.6 mg and 12.5 mg to 37.5 mg respectively. When administering these medications it is important to consider the half life. The initial injections are designed to obtain immediate and high levels of anticholinergic activity. The maintenance regimen will be responsible for maintaining low levels of anticholinergic activity during the remainder of the withdrawal period.

Initially, patients are given an inter muscular dose of a 3.0 cc solution containing 0.4 mg atropine. 0.4 mg scopolamine, 12.5 mg chlorpromazine and 0.5 cc Xylocaine(2%). The dosage may vary to accommodate age, weight, physical constitution and level of addiction. A therapeutic dosage may range from a total volume of 1.4 cc to 3.0 cc. with 0.8 cc maintained for subcutaneous injection 0.4 cc behind each ear. The patient will be checked after five minutes in a darkened room for a possible adverse reaction, indicated by pupils that are fixed and dilated.

Pupillary response is examined after the patient has been in a darkened room for a minimum of five minutes. If the pupils are normal and reactionary, the physician administers subcutaneous injections of the remaining solution in a volume of 0.3 to 0.4 cc behind each ear. These injection sites provide for rapid onset because the tributaries of the veins, in this region, contain, no valves.

Patients are to be observed for an additional five minutes to insure a therapeutic dose. Patients should experience slight euphoria, dilated pupils and xerostomia.

For patients of substantial size, level of addiction or who had experienced higher than expected levels of withdrawal symptoms, the amounts of atropine and chlorpromazine may be increased at this time with a secondary inter muscular injection from about 0.1 mg to 0.6 mg and 12.5 mg to 37.5 mg respectively.

Typically, following treatment the patient experiences slight euphoria, dilated pupils with difficulty in focusing from near to far and xerostomia. The effects become most pronounced in the period from 30 minutes to 1½ hours post treatment. These effects will dissipate in a period of six to eight hours.

Nicotine itself will leave the body in up to three days. Patients are instructed to drink at least one quart of water per day to help facilitate this exit. The increased levels of acetylcholine may take as long as two weeks to revert back to normal. As a consequence, an adjunct therapy is prescribed. The follow up consists of standard dosages of oral anticholinergic, scopolamine patches and benzodiazepine. Should the patient be currently taking Clonidine, antidepressants or other medications that suppress or excite MFB activity, the benzodiazepine may be withheld.

Behavioral therapy is employed prior to and after the administration of the medications through audio tapes, compact discs, CD ROM, and video tapes. Replacing the habits of smoking, with the new behaviors, occurs much more easily; when the patient is aware and has forethought of the habits associated with smoking.

Studies have shown that when this method is implemented, as herein described, after two months, eighty-three percent of a random sampling of 187 patients remain non-smokers. Patients that could not be reached or refused contact were assumed to be smoking.

Further, after the twelfth month of such patients, sixty-four percent remain non-smokers. Patients that could not be reached or refused contact were assumed to be smoking.

With respect to the above description then, it is to be realized that the optimum method for the present invention may include variations in the amount of medication and the types of behavioral therapy; however, for one skilled in the art, such variations are deemed readily apparent and obvious, and all equivalent relationships to those described in the specification are intended to be encompassed by the present invention.

What is claimed is:

1. A method of helping a patient eliminate tobacco dependency, comprising the steps of:

injecting said patient with solution of anticholinergic medications from about 1.0 cc to 6.0 cc containing atropine ranging from 0.1 mg to 0.8 mg, scopolamine ranging from 0.1 mg to 0.6 mg, chlorpromazine ranging from 1 mg to 50 mg in a suitable carrier; and Prescribing, concomitantly, to said patient a therapeutic dose of anticholinergic medications using accepted pharmacological principals; and Prescribing concomitantly to said patient a therapeutic dose of Benzodiazepines using accepted pharmacological principals.

2. A method of helping a patient eliminate tobacco dependency, comprising the steps of:

injecting said patient with solution of anticholinergic medications from about 1.0 cc to 6.0 cc containing atropine ranging from 0.1 mg to 0.8 mg, scopolamine ranging from 0.1 mg to 0.6 mg, chlorpromazine ranging from 1 mg to 50 mg in a suitable carrier; and Prescribing, concomitantly, to said patient a therapeutic dose of anticholinergic medications using accepted pharmacological principals; and Prescribing concomitantly to said patient a therapeutic dose of Benzodiazepines using accepted pharmacological principals; and implementing cognitive reconstructional behavioral therapy; and implementing cognitive underlying resistance behavioral therapy; and implementing core transformational behavioral therapy.

3. A method of helping a patient eliminate tobacco dependency, comprising the steps of:

Establish a therapeutic dose of dopaminergic and or serotonin agonist or antagonist medications using accepted pharmacological principals; and injecting said patient with solution of anticholinergic medications from about 1.0 cc to 6.0 cc containing atropine ranging from 0.1 mg to 0.8 mg, scopolamine ranging from 0.1 mg to 0.6 mg, chlorpromazine ranging from 1 mg to 50 mg in a suitable carrier; and Prescribing, concomitantly, to said patient a therapeutic dose of anticholinergic medications using accepted pharmacological principals.

4. A method of helping a patient eliminate tobacco dependency, comprising the steps of:

Establish a therapeutic dose of dopaminergic and or serotonin agonist or antagonist medications using accepted pharmacological principals; and injecting said patient with solution of anticholinergic medications from about 1.0 cc to 6.0 cc containing atropine ranging from 0.1 mg to 0.8 mg, scopolamine ranging from 0.1 mg to 0.6 mg, chlorpromazine ranging from 1 mg to 50 mg in a suitable carrier; and Prescribing, concomitantly, to said patient a therapeutic dose of anticholinergic medications using accepted pharmacological principals; and implementing cognitive reconstructional behavioral therapy; and implementing cognitive underlying resistance behavioral therapy; and implementing core transformational behavioral therapy.

5. A method in claim 1, wherein the carrier is a solution containing procaine or other suitable carrier for the injection of pharmaceuticals.

6. A method of claim 1, wherein at least 1 injection of at least 1.0 cc is injected into patient.

7. A method of claim 1, wherein 0.3 to 0.4 cc. volume are injected subcutaneously behind each ear in the area of the mastoid.

8. A method of claim 1, wherein said anticholinergic medications include an oral regimen of anticholinergics and transdermal scopolamine patches.

9. A method of claim 1, wherein said anticholinergic medications may be administered upon the initial office visit.

10. A method of claim 2, wherein a combination of behavioral therapies are implemented to interrupt habitual physical and emotional patterns reinforced by the concomitant experience of physical and emotional pleasure.

11. A method of claim 2, wherein a combination of behavioral therapies are implemented to interrupt habitual physical and emotional patterns reinforced by the concomitant experience of physical pleasure.

12. A method of claim 2, wherein a combination of behavioral therapies are implemented to interrupt habitual physical and emotional patterns reinforced by the concomitant experience of emotional pleasure.

13. A method of claim 3, wherein the patient may be preconditioned for treatment with psychotropic medications of other pharmaceutical compounds having the affect of reducing anxiety or depression.

* * * * *